United States Patent [19]

Russell et al.

[11] Patent Number: 5,586,161

[45] Date of Patent: Dec. 17, 1996

[54] METHOD OF MEASUREMENT OF ABNORMAL WEAR DEBRIS AND PARTICULATE CONTAMINATION IN MACHINE COMPONENTS BY OIL ANALYSIS

[75] Inventors: Henry J. Russell; Brenton P. Hill, both of Jabiru, Australia

[73] Assignee: Energy Resources of Australia Ltd., Australia

[21] Appl. No.: 292,560

[22] Filed: Aug. 18, 1994

[51] Int. Cl.$^6$ .................................................. G01N 23/223
[52] U.S. Cl. .................................................. 378/45; 378/47
[58] Field of Search ........................................ 378/45, 47

[56] References Cited

U.S. PATENT DOCUMENTS 3,751,661  8/1973  Packer et al. .............................. 378/47
4,020,676  5/1977  Nuxhall et al. .

OTHER PUBLICATIONS

Australian Patent Application No. 52995/1986 In The Name Of Coal.
Australian Patent Application No. 55742/1990 In The Name Of Coal.

*Primary Examiner*—Craig E. Church
*Attorney, Agent, or Firm*—Poms, Smith Lande & Rose

[57] ABSTRACT

A method of measurement of abnormal wear debris and particulate contamination in machine components by oil analysis comprising the steps of:

passing oil through a filter of selected pore size such that the filter entraps most larger abnormal wear particles and excludes most smaller normal wear particles;

placing the filter in an x-ray spectrometer; and converting the measured x-ray intensities of the particles trapped in the filter to a quantitative value indicating the species and concentration of abnormal wear particles and contamination particles in the oil.

5 Claims, No Drawings

METHOD OF MEASUREMENT OF ABNORMAL WEAR DEBRIS AND PARTICULATE CONTAMINATION IN MACHINE COMPONENTS BY OIL ANALYSIS

The present invention relates to the measurement of abnormal wear debris and particulate contamination in machine components by oil analysis.

The invention has been developed primarily for use in quantitatively determining the wear of machine components and will be described hereinafter with reference to this application.

Measurement of wear in machine components is well known and is essential to any predictive maintenance program. Generally speaking, there are two options in determining machine component wear. Firstly, the machine can be disassembled and wearing surfaces visually examined for signs of wear. This option has the obvious drawbacks of high labour costs and downtime on the machinery.

Secondly, it is possible to analyse the oil for its concentration of metallic particles and contamination from external sources such as dust. Two of the most commonly used methods of oil analysis are:
1) Spectrographic Analysis
2) Filtergram Microscopy In standard spectrographic analysis, the oil sample is diluted and aspirated into an energy source which excites the wear metals to give optical emissions at visible wavelengths. The energy source is an inductively coupled argon plasma or electric arc.

This type of spectrographic analysis is designed to measure elements in solution, and it cannot detect particles larger than about five micrometers. Particles smaller than five micrometers represent normal wear and are usually of no concern. Abnormal wear particles are much bigger, usually up to one hundred micrometers and even larger in severe cases.

The large particles can be measured by acid digestion-spectrographic analysis, but this is very slow and tedious. This measurement produces total concentration, of which abnormal wear may be only a small percentage. Hence, the detection of a small (but significant) quantity of abnormal wear debris may be swamped by a much larger mass of normal wear particles.

Despite the disadvantages, spectrographic analysis of the above type is commonly employed in the industry.

Filtergram microscopy uses an optical microscope to observe the particles in the oil. The oil sample is diluted, and passed through a cellulose nitrate membrane filter with a pore size selected to exclude most normal wear particles. The filter is clarified using a proprietary reagent and mounted on a glass microscope slide.

The particles are then viewed on a microscope using both transmitted and reflected light, and colour filters are used to improve definition. Preparation of the slides is very rapid, but the microscopic examination is tedious, requiring a comprehensive scan of the whole filtergram with a very small field-of-view.

Observing the colour, reflectivity, shape and topography of the particles can provide information about the mechanism and severity of abnormal wear, but not its elemental composition. The output is only semi-quantitative (high-medium-low) and is difficult to trend arithmetically. It is, however, an excellent diagnostic tool and is generally thought to be superior in detecting serious malfunctions to spectrographic analysis.

The existing methods of detecting abnormal wear all have disadvantages and it is an object of the invention to ameliorate at least some of these deficiencies of the prior art.

According to the invention there is provided a method of measurement of abnormal wear debris and particulate contamination in machine components by oil analysis comprising the steps of:

passing oil through a filter of selected pore size such that the filter entraps most larger abnormal wear particles and excludes most smaller normal wear particles;

placing the filter in an x-ray spectrometer; and converting the measured x-ray intensities of the particles trapped in the filter to a quantitative value indicating the species and concentration of abnormal wear particles and contamination particles in the oil.

X-ray spectrometry is capable of detecting the larger wear particles. It also detects particulate contamination such as dust. In this regard dust comprises silica, aluminium and iron in ratios dependent on the geographical source of the dust. These components give a recognisable signature spectrometer reading.

Preferably, the filter is clarified using a proprietary reagent and is mounted on a optically transparent slide which remains clear and colourless after exposure to x-rays. The slide should be chemically pure with respect to the elements being determined, although some trace impurities can be tolerated as long as they are homogenously dispersed throughout the batch of slides.

Preferably also, if the quantitative value exceeds a flag value the slide is mounted directly into an optical microscope for further processing by visual examination.

Preferably also, the slide is an acrylic plastic.

Preferably also, the filter is a cellulose nitrate membrane.

Preferably also, the filter has a pore size of approximately three micrometers.

The invention will now be described by way of illustration only with reference to an example.

A sample of approximately 70 mL of oil is taken from a compartment using classical sampling techniques, and placed in a 100 mL screw top plastic bottle.

The bottle is placed in a constant temperature ultrasound bath and heated to 50°. Ultrasonic vibration is used to re-suspend particles which may have settled.

The sample is agitated vigorously for a few seconds by contacting the bottle with the head of a vortex mixer, and a 1 mL subsample is withdrawn using a micro pipette.

The subsample is transferred to a culture tube and mixed with 1 mL of Shell X55 solvent using the vortex mixer.

The mixture is transferred to a glass syringe outer, and Shell X55 solvent is used to wash any residual sample from the culture tube into the syringe outer.

A vacuum pump is turned on to suck the mixture through a membrane filter which is mounted in a 13 mm filter holder onto the Luer tip of the glass syringe outer.

The suction is stopped, and 10 mL of Shell X55 solvent is dispensed into the glass syringe outer. Suction is then reapplied to draw the solvent through the filter, thus washing away any trace of oil, leaving only particles on the filter.

The membrane filter is removed from the holder and placed on the edge of a plastic slide to dry. The slide is a clear, colourless acrylic or other suitable polymer and remains clear and colourless after exposure to x-rays. About one minute is allowed for the solvent to evaporate from the filter.

One drop of "Super Sepra Clear Clarifying Solution" (Gelman Sciences) is placed on the centre of the slide, and the filter is placed on top of the solution, which soaks in to the membrane.

The slide is placed in a hot air oven and baked at 90° for nine minutes.

When cool, the slide is loaded into the x-ray spectrometer and analysed to determine the species and concentration of the particles on the slide. Standard x-ray emission lines are used, and intensities are converted to concentrations via calibration standards prepared as described below.

The measured concentrations are compared to predetermined allowable limits for the compartment from which the sample was taken. If the limit is exceeded for any of the elements being determined, the slide is transferred to the optical microscope for further examination using conventional filtergram techniques.

Calibration standards are prepared by dispensing onto membrane filters, 10 μL aliquots of solutions of varying concentrations of the elements to be analysed. A microsyringe can be used for this purpose. The filters are air dried and processed as above.

Although the invention has been described with reference to a particular example, it will be appreciated by those skilled in the art that the invention may be embodied in many other forms.

We claim:

1. A method of measuring abnormal wear of machine components by oil analysis comprising the steps:

taking a sample of a predetermined amount of the oil from the machine and placing it in a closable container;

re-suspending particles within said oil sample by applying ultrasonic vibrations to said bottle followed by vigorous agitation of said container;

withdrawing a subsample from said container;

passing said subsample through a filter of selected pore size;

removing any remaining oil from said filter by applying solvents;

drying said filter;

mounting said filter on a transparent slide;

clarifying said filter using a reagent;

analysing said slide using x-ray spectrometer; and further analyzing said filter using filtergram microscopy.

2. The method of claim 1, wherein the slide remains clear and colorless after exposure to x-rays.

3. The method of claim 1, wherein the slide is an acrylic plastic.

4. The method of claim 1, wherein the filter is a cellulose nitrate membrane.

5. The method of claim 1, wherein the filter has a pore size of approximately three micrometers.

* * * * *